US012746220B2

(12) United States Patent
Yoon et al.

(10) Patent No.: US 12,746,220 B2
(45) Date of Patent: Sep. 29, 2026

(54) PHARMACEUTICAL COMPOSITION FOR TREATMENT OR PREVENTION OF ISCHEMIC CARDIOVASCULAR DISEASE

(71) Applicant: INDUSTRY-ACADEMIC COOPERATION FOUNDATION, YONSEI UNIVERSITY, Seoul (KR)

(72) Inventors: Young Sup Yoon, Seoul (KR); Ki Bum Lee, Monmouth Junction, NJ (US); Hyeon Yeol Cho, Seoul (KR); Sy-Tsong Chueng, Piscataway, NJ (US)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 325 days.

(21) Appl. No.: 16/769,196

(22) PCT Filed: Nov. 2, 2018

(86) PCT No.: PCT/KR2018/013278

§ 371 (c)(1),
(2) Date: Jun. 2, 2020

(87) PCT Pub. No.: WO2019/088772

PCT Pub. Date: May 9, 2019

(65) Prior Publication Data

US 2021/0369653 A1 Dec. 2, 2021

(30) Foreign Application Priority Data

Nov. 2, 2017 (KR) ........................ 10-2017-0145305
Sep. 17, 2018 (KR) ........................ 10-2018-0111077

(51) Int. Cl.

| | |
|---|---|
| ***A61K 31/19*** | (2006.01) |
| ***A61K 9/51*** | (2006.01) |
| ***A61K 38/10*** | (2006.01) |
| ***A61K 38/17*** | (2006.01) |
| ***A61K 47/59*** | (2017.01) |
| ***A61K 47/69*** | (2017.01) |
| ***A61P 9/10*** | (2006.01) |
| ***C07D 403/14*** | (2006.01) |
| ***C07K 7/08*** | (2006.01) |
| ***C07K 14/47*** | (2006.01) |
| *A61K 38/00* | (2006.01) |

(52) U.S. Cl.
CPC ............ *A61K 31/19* (2013.01); *A61K 9/5115* (2013.01); *A61K 38/10* (2013.01); *A61K 38/179* (2013.01); *A61K 47/595* (2017.08); *A61K 47/6929* (2017.08); *A61P 9/10* (2018.01); *C07D 403/14* (2013.01); *C07K 7/08* (2013.01); *C07K 14/4705* (2013.01); *A61K 38/00* (2013.01); *C07K 2319/09* (2013.01); *C07K 2319/80* (2013.01)

(58) Field of Classification Search
None
See application file for complete search history.

(56) References Cited

U.S. PATENT DOCUMENTS

2010/0316702 A1 12/2010 Briggs et al.
2017/0130204 A1 * 5/2017 Kim .......................... A61P 9/10

FOREIGN PATENT DOCUMENTS

| | | | |
|---|---|---|---|
| JP | 5897002 | B2 | 4/2016 |
| KR | 1020150104049 | A | 9/2015 |
| WO | 2017015246 | A1 | 1/2017 |

OTHER PUBLICATIONS

Pearson W ('An introduction to sequence similarity ("Homology") searching' Curr Protoc Bioinformatics Jun. 2013 printed as pp. 1-9) (Year: 2013).*
Matsumoto et al. ('Fish-bite structure by three-dimensional hydrogen-bond acceptor: IR spectroscopy of pyrrole and N-methylpyrrole binary clusters' The Journal of Chemical Physics v137 2012 pp. 1-7) (Year: 2012).*
Pandian, G.N., et al, "A synthetic small molecule for rapid induction of multiple pluripotency genes in mouse embryonic fibroblasts", Scientific Reports, 2012, vol. 2, No. 544, pp. 1-8, see abstract p. 1.
Patel S et al. "Nanoscript: A nanoparticle-based artificial transcription factor for effective gene regulation", ASC Nano, 2014 vol. 8, No. 9, pp. 8959-8967, See abstract 8959-8961, 8965, S-8; figure 1; table S-1.

* cited by examiner

*Primary Examiner* — Ronald T Niebauer
(74) *Attorney, Agent, or Firm* — ROTHWELL, FIGG, ERNST & MANBECK, P.C.

(57) ABSTRACT

Provided in the present specification is an ETV2 transcription factor comprising: a polyamide comprising a domain binding to DNA (DNA binding domain) of an ETV2 gene; a nuclear localization signal peptide; and a nano-particle.

10 Claims, 17 Drawing Sheets

Specification includes a Sequence Listing.

PHARMACEUTICAL COMPOSITION FOR TREATMENT OR PREVENTION OF ISCHEMIC CARDIOVASCULAR DISEASE

RELATED APPLICATIONS

This application is a U.S. national phase entry of, and claims priority to, PCT International Phase Application No. PCT/KR2018/013278, filed Nov. 2, 2018, which claims priority to Korean Patent Application No. KR 10-2018-0111077, filed Sep. 17, 2018, and Korean Patent Application No. KR 10-2017-0145305, filed Nov. 2, 2017.

The entire contents of the above-referenced applications and of all priority documents referenced in the Application Data Sheet filed herewith are hereby incorporated by reference for all purposes.

INCORPORATION-BY-REFERENCE OF SEQUENCE LISTING

This application is being filed along with a Sequence Listing in electronic format. The Sequence Listing is provided as a file titled 17PD5897PCT-US_Sequence.txt, which is 1,102 bytes in size, last modified on Mar. 21, 2024.

TECHNICAL FIELD

The present disclosure relates to a pharmaceutical composition for treatment or prevention of an ischemic cardiovascular disease. More specifically, the present disclosure relates to a pharmaceutical composition that provides a therapeutic effect on an ischemic tissue by overexpressing a transcription factor specific to blood-vessel formation in the ischemic tissue.

BACKGROUND ART

An ischemic cardiovascular disease is one of diseases with high prevalence and mortality due to lack of oxygen and nutrient supply through a blood-vessel. This ischemic cardiovascular disease is on the rise worldwide.

Accordingly, for treatment of the ischemic cardiovascular disease, chemotherapy has been proposed. However, because a damaged or defective heart may not be recovered by itself, the chemical treatment for the ischemic cardiovascular disease only delays progression of the disease. Heart transplantation may be a fundamental therapy for recovery of a cardiac function. However, the heart transplantation may cause problems such as lack of heart providers, medical ethics, and physical and economic burdens of patients.

In one example, as a new strategy for treatment of the ischemic cardiovascular disease, a regenerative treatment to form a blood-vessel by inducing neovascularization to create a new blood-vessel from stem cells has been proposed as an alternative treatment. In the blood-vessel regeneration treatment using the stem cell treatment, adult stem cells are mainly used for research. However, the treatment using the adult stem cells may have insufficient effect in several clinical trials. The effectiveness of the treatment with the adult stem cells in clinical application thereof to a peripheral blood-vessel disease has not been proven. The weak therapeutic effect of the cell therapy using the adult stem cells may be due to inherent limitations of the adult stem cells, or deteriorated ability thereof differentiating into target cells such as vascular endothelial cells and myocardial cells.

Accordingly, there is a continuous need to develop a blood-vessel regenerative treatment method using stem cells, which may overcome the above limitations and effectively treat the ischemic cardiovascular disease.

This “Background Art” section has been set forth to facilitate understanding of the present disclosure. It should be understood that the contents described in this section are not recognized as a prior art.

DISCLOSURE

Technical Problem

Pluripotent stem cells may be self-proliferating and may differentiate into various cells and may be used for blood-vessel regeneration treatment. Accordingly, as a new strategy to restore an ischemic tissue function, a blood-vessel regeneration treatment method using vascular endothelial cells differentiated from embryonic stem cells (ES cells) isolated from embryos and induced pluripotent stem cells made from somatic cells has been proposed.

Further, the present inventors have recognized that potential risk factors of pluripotent stem cells, such as development of tumors and abnormal tissues, use of animal components used in differentiation processes thereof, a low differentiation thereof into vascular endothelial cells, etc., cause side effects in the blood-vessel regenerative therapy or insignificant therapeutic effects.

Thus, the present inventors have focused on direct cellular reprogramming in which overexpressing cells or tissue-specific transcription factor genes in the adult somatic cells allows adult somatic cells to be directly reprogramed to somatic cells of other lineages without going through a pluripotent state.

As a result, the present inventors have found that overexpressing ETV2 as a blood-vessel formation-specific transcription factor in the fibroblast allows the fibroblast to be directly reprogrammed into a vascular endothelial cell without going through a pluripotent state.

In particular, the present inventors used an ETV2 transcription factor which mimics ETV2 and thus was able to solve a problem in a clinical application of a retrovirus or lentivirus-mediated gene injection method used conventionally for overexpression of the transcription factor, due to insertional mutation occurring in a genome of cells when using the injection method.

Accordingly, a purpose of the present disclosure is to provide an ETV2 transcription factor which may be injected into a human somatic cell such as a fibroblast to reprogram directly the human somatic cell to a vascular endothelial cell, and to provide a preparation method thereof.

Another purpose of the present disclosure is to provide a pharmaceutical composition for treatment or prevention of an ischemic cardiovascular disease, the composition containing the ETV2 transcription factor and being clinically applicable to an ischemic tissue, and inducing neovascularization of directly reprogrammed vascular endothelial cells in the ischemic tissue to which the composition is injected.

Another purpose of the present disclosure is to provide a method for directly reprogramming human somatic cells to vascular endothelial cells, the method comprising injecting the ETV2 transcription factor into the human somatic cells, and obtaining a differentiated directly reprogrammed vascular endothelial cell.

Another purpose of the present disclosure is to provide a method of treating an ischemic cardiovascular disease, the method comprising injecting the ETV2 transcription factor into an ischemic tissue of a mammal other than humans.

The purposes of the present disclosure are not limited to those mentioned above. Other purposes as not mentioned will be clearly understood by those skilled in the art from the following description.

Technical Solution

According to one embodiment of the present disclosure, an ETV2 transcription factor is provided, containing polyamide containing a domain binding to DNA (DNA binding domain) of an ETV2 gene, a nuclear localization signal peptide, and a nano-particle.

As used herein, the term "ETV2 transcription factor" may refer to an artificial transcription factor as synthesized to bind to the ETV2 gene and activate transcription thereof. Accordingly, the expression of the ETV2 gene may be promoted by the ETV2 transcription factor in cells into which the ETV2 transcription factor has been added.

The ETV2 transcription factor in accordance with the present disclosure may have a structure in which a polyamide containing the DNA binding domain for the ETV2 gene and a nuclear localization signal peptide are attached onto a surface of the nano-particle.

As used herein, the term, "ETV2 gene" is a gene associated with blood-vessel formation and may specifically be a gene expressed in a specific manner to vascular endothelial cells.

Thus, as used herein, the term, "DNA binding domain for the ETV2 gene" may refer to a domain that may complementarily bind to a binding site of the ETV2 gene.

In this connection, the term "polyamide containing DNA binding domain for an ETV2 gene" may refer to a polyamide compound having a hairpin structure containing pyrrole and imidazole sequences forming a hairpin structure, and DMAPA (dimethylaminopropylamine). For example, the polyamide may have a sequence of PyPyβImImPyImPyPyβPyPyβ-DMAPA. However, the present disclosure is not limited thereto. As long as the polyamide has DNA binding to the ETV2 gene, the polyamide may have more various structures.

As used herein, the term, "nuclear localization signal peptide" may mean a peptide having a domain present in a primary structure of a protein to be synthesized in cells and transferred to the nucleus. Thus, the nuclear localization signal peptide may promote influx of the ETV2 transcription factor into the nucleus of the cell. In this connection, the nuclear localization signal peptide may have 70% or greater homology with an amino acid sequence represented by SEQ ID NO: 2. Preferably, the nuclear localization signal peptide may have 80% or greater homology with the amino acid sequence represented by SEQ ID NO: 2. More preferably, the nuclear localization signal peptide may have 90% or greater homology with the amino acid sequence represented by SEQ ID NO: 2. More preferably, the nuclear localization signal peptide may have 100% homology to the amino acid sequence represented by SEQ ID NO: 2.

Further, as used herein, the term, "nano-particle" may be a metal particle having a nano size. In this connection, the nano-particle may be at least one of a gold nano-particle, a magnetic nuclear gold nano-particle, a silver nano-particle, and a tin nano-particle. Preferably, the nano-particle may be a magnetic nuclear gold nano-particle. However, the present disclosure may not be limited thereto. As long as the nano-particle may enter the nucleus of the target cell, and the polyamide containing the DNA binding domain for the ETV2 gene and the nuclear localization signal peptide as aforementioned may be attached thereto, the nano-particle may include various types of particles.

In one example, when the nano-particle is the magnetic nuclear gold nano-particle, the ETV2 transcription factor in which the magnetic nuclear gold nano-particle is located at a center thereof may move to the target cell using magnetism, and may overexpress the ETV2 gene in the target cell without using a genetic material such as a virus or DNA plasmid. Furthermore, the ETV2 transcription factor containing nano-particles may be real time tracked non-invasively via Raman/dark-field imaging. Thus, MRI may be used to track presence and a location of the ETV2 transcription factor-introduced cells in vivo.

According to one embodiment of the present disclosure, the ETV2 transcription factor may further contain an active peptide that further contains a transcription activation domain of the ETV2 gene.

As used herein, the term, "transcription activation domain of the ETV2 gene" may mean a domain that initiates transcription of the ETV2 gene when the DNA binding domain is bound to the ETV2 gene, thereby activating expression of the ETV2 gene in the cell.

In this connection, "active peptide containing transcription activation domain of the ETV2 gene" may be a peptide containing the transcription activation domain of the ETV2 gene. In one example, the active peptide may have 70% or greater homology with an amino acid sequence represented by SEQ ID NO: 1. Preferably, the active peptide may have 80% or greater homology with the amino acid sequence represented by SEQ ID NO: 1. More preferably, the active peptide may have 90% or greater homology with the amino acid sequence represented by SEQ ID NO: 1. More preferably, the active peptide may have 100% homology to the amino acid sequence represented by SEQ ID NO: 1.

In this connection, the active peptide together with the polyamide containing the DNA binding domain for the ETV2 gene and the nuclear localization signal peptide as above-described may be bound to the nano-particle surface.

According to one embodiment of the present disclosure, the ETV2 transcription factor may further contain a plurality of MUAs (mercaptoundecanoic acids). In this connection, the plurality of MUAs may be configured to connect at least one of the polyamide, the active peptide and the nuclear localization signal peptide to the nano-particles.

More specifically, the MUA may act as a linker that binds to functional polymers such as at least one of the polyamide, the active peptide and the nuclear localization signal peptide and attaches the functional polymer to the nano-particle surface. For example, the MUA may bind to the functional polymer such as at least one of the active peptide and the nuclear localization signal peptide via EDC (1-ethyl-3-(3-dimethylaminopropyl)-carbodiimide) and/or NHS (N-hydroxy succinimide).

According to one embodiment of the present disclosure, the polyamide may have a surface area of 4 to 10% relative to an entire surface area of the nano-particle. Preferably, the polyamide may have a surface area of 7 to 9% relative to the entire surface area of the nano-particle. More preferably, the polyamide may have a surface area of 9% relative to the entire surface area of the nano-particle. However, the present disclosure is not limited thereto.

According to one embodiment of the present disclosure, the nuclear localization signal peptide may have a surface area of 60 to 75% relative to the entire surface area of the nano-particle. Preferably, the nuclear localization signal peptide may have a surface area of 65 to 70% relative to the entire surface area of the nano-particle. More preferably, the nuclear localization signal peptide may have a surface area of 66 to 69% relative to the entire surface area of the nano-particle. However, the present disclosure is not limited thereto.

According to one embodiment of the present disclosure, the active peptide may have a surface area of 20 to 30% relative to the entire surface area of the nano-particle. Preferably, the active peptide may have a surface area of 21 to 25% relative to the entire surface area of the nano-particle. More preferably, the active peptide may have a surface area of 22 to 24% relative to the entire surface area of the nano-particle. However, the present disclosure is not limited thereto.

According to one embodiment of the present disclosure, the ETV2 transcription factor may further contain a SAHA (suberanilo-hydroxamic acid-ammonium-adamatane) derivative, or a CTB (N-(4-Chloro-3-(trifluoromethyl) phenyl)-2-ethoxybenzamide) derivative.

In this connection, the SAHA derivative may inhibit activity of HDAC (histone deacetylase). The CTB derivative may promote activity of HAT (histone acetyl transferase).

According to one embodiment of the present disclosure, a method of preparing an ETV2 transcription factor is provided, comprising mixing, with MUA (mercaptoundecanoic acid), each of functional polymers composed of the polyamide acting as the DNA binding domain for the ETV2 gene, the active peptide acting as a transcription activation domain of the ETV2 gene, and the nuclear localization signal peptide to form each mixture, adding EDC (1-ethyl-3-(3-dimethylaminopropyl)-carbodiimide) and NHS (N-hydroxy succinimide) to the mixture to form a conjugate between the polyamide and the MUA, a conjugate between the active peptide and the MUA, and a conjugate between the nuclear localization signal peptide and MUA, respectively, and reacting each of the conjugates with a nano-particle to form the ETV2 transcription factor.

In this connection, the mixing may comprise mixing, with each MUA, the polyamide at a content of 4 to 10% relative to a total amount of the functional polymers, the active peptide at a content of 20 to 30% relative to a total amount of the functional polymers, and the nuclear localization signal peptide at a content of 60 to 75% relative to a total amount of the functional polymers.

Thus, in the ETV2 transcription factor, the conjugate between the polyamide and MUA as attached to the nano-particles may have a content of 4 to 10% based on a total amount of conjugates between the functional polymers-MUAs. Furthermore, in the ETV2 transcription factor, the conjugate between the active peptide and the MUA as attached to the nano-particle may have a content of 20 to 30% based on a total amount of conjugates between the functional polymers-MUAs. Furthermore, in the ETV2 transcription factor, the conjugate between the nuclear localization signal peptide and the MUA as attached to the nano-particle may have a content of 60 to 75% based on a total amount of conjugates between the functional polymers-MUAs.

According to one embodiment of the present disclosure, the method may further comprise adding SAHA or CTB to the ETV2 transcription factor.

In one example, the ETV2 transcription factor may be injected into human somatic cells such as fibroblasts to directly reprogram skin fibroblasts to vascular endothelial cells with neovascularization ability. In this connection, the directly reprogrammed vascular endothelial cell differentiated by the ETV2 transcription factor may be obtained by expressing vascular endothelial cell-specific genes (e.g., ETV2 gene) that were conventionally not expressed from the fibroblast as a source cell. Thus, the directly reprogrammed vascular endothelial cells differentiated by the ETV2 transcription factor may be used as a cell therapy composition to be implanted into the ischemic tissue. Furthermore, the ETV2 transcription factor may be used as a pharmaceutical composition for treatment or prevention of an ischemic cardiovascular disease that may be injected into a local site of an ischemic disease.

According to one embodiment of the present disclosure, a pharmaceutical composition for treatment or prevention of an ischemic cardiovascular disease, the composting containing the ETV2 transcription factor, is provided.

As used herein, the term “ischemic cardiovascular disease” may refer to a disease that occurs when the artery is narrowed or blocked, and thus sufficient blood supply to a heart muscle is not achieved. The ischemic cardiovascular disease disclosed in the present specification may be interpreted in the same meaning as ischemic heart diseases.

Further, according to one embodiment of the present disclosure, a pharmaceutical composition for treating or preventing an ischemic cardiovascular disease, the composition containing the ETV2 transcription factor, is provided.

In this connection, the pharmaceutical composition may be provided as a cell therapeutic agent. For example, the pharmaceutical composition according to the present disclosure may be implanted in a defect site or an adjacent site thereto for recovery of an ischemic tissue.

Furthermore, the pharmaceutical composition according to the present disclosure may further contain the directly reprogrammed vascular endothelial cells differentiated by the ETV2 transcription factor.

Accordingly, the pharmaceutical composition according to the present disclosure containing the directly reprogrammed vascular endothelial cells differentiated by the ETV2 transcription factor may be injected into a defective site or an adjacent site thereof for recovery of an ischemic tissue.

In one example, the pharmaceutical composition according to the present disclosure may be administered in a manner of at least one of intravenous injection, intramuscular injection, subcutaneous injection, intradermal injection, intratracheal injection, or topical skin application. However, a formulation of the pharmaceutical composition according to one embodiment of the present disclosure is not limited thereto. The composition may be formulated in various forms according to any route of administration and any mode of administration as long as the cell therapeutic agent composition may reach a target site.

When the pharmaceutical composition according to the present disclosure is formulated in a form of a sterile injectable solution, the solution may further contain suspensions, dissolution aids, stabilizers, isotonic agents, preservatives, adsorption inhibitor, surfactants, diluents, pH adjusters, painless agents, buffers, sulfur reducing agents, or antioxidants. Further, when the pharmaceutical composition according to the present disclosure is formulated into an external application formulation, the pharmaceutical composition may be applied to an organ or a skin as an individual therapeutic agent or may be applied in combination with other therapeutic agents, and may be administered sequentially or simultaneously with conventional therapeutic agents. In the administration of the pharmaceutical composition according to the present disclosure to the ischemic tissue, it is important to administer an effective amount of the composition that may achieve the maximum effect in a minimal amount without side effects, while taking into account all of the above factors. The dosage and application amount of the pharmaceutical composition according to the present disclosure may be easily determined by those skilled in the art.

According to one embodiment of the present disclosure, a preparation method of the directly reprogrammed vascular endothelial cells used as the composition for cell therapeutic agent is provided.

According to one embodiment of the present disclosure, the method for preparing the vascular endothelial cell may comprise injecting the ETV2 transcription factor into skin fibroblast and differentiating directly reprogrammed vascular endothelial cells.

In this connection, the injection method of the ETV2 transcription factor may be different from the retrovirus and lentivirus-mediated gene injection method. Accordingly, the cell therapeutic agent composition according to one embodiment of the present disclosure may have clinical stability applicable to the ischemic tissue.

According to one embodiment of the present disclosure, there is provided a method for treating an ischemic cardiovascular disease, the method comprising injecting the ETV2 transcription factor in accordance with the present disclosure into an ischemic tissue of a mammal other than humans.

In this connection, the ETV2 transcription factor may be injected into a host suffering from damage to blood-vessels, for example, mammals other than humans. Specifically, in the treatment method of the ischemic cardiovascular disease according to the present disclosure, the ETV2 transcription factor may be applied to a host having heart failure, heart attack, coronary artery disease, myocardial disease, limited cardiomyopathy, or hypertrophic cardiomyopathy. Furthermore, the ETV2 transcription factor may be injected into a host having clinical symptoms of brain blood-vessel disease, diabetes complications, and wounds.

According to one embodiment of the present disclosure, the injecting the ETV2 transcription factor may further comprise injecting the directly reprogrammed vascular endothelial cells differentiated by the ETV2 transcription factor into mammalian ischemic tissue other than humans.

That is, the directly reprogrammed vascular endothelial cells differentiated by the ETV2 transcription factor may be injected into the ischemic tissue of the host as a cell therapeutic agent.

An application scope of the pharmaceutical composition according to the present disclosure is not limited thereto. The pharmaceutical composition according to the present disclosure may be applied to more various diseases caused by ischemia of tissue.

Hereinafter, the present disclosure will be described in more detail based on examples. However, these examples are only for illustrative purposes, and a scope of the present disclosure should not be interpreted as being limited to these examples.

Advantageous Effects

The present disclosure may realize the ETV2 transcription factor and the preparation method thereof and may realize an efficient differentiation method into vascular endothelial cells, in which the skin fibroblast as a source cell may be directly reprogrammed to vascular endothelial cells without going through a pluripotent state.

Thus, according to the present disclosure, the side effects of the blood-vessel regeneration treatment and the slight therapeutic effect as caused by potential risk factors of pluripotent stem cells, such as the development of tumors and abnormal tissues, the use of animal components used in differentiation processes, and the low differentiation into vascular endothelial cells may be removed.

Furthermore, the present disclosure may realize the ETV2 transcription factor clinically applied directly to the ischemic tissue to overexpress the ETV2 gene. Thus, the ETV2 transcription factor according to the present disclosure has an effect of solving the problem in a clinical application of a retrovirus or lentivirus-mediated gene injection method used conventionally for overexpression of the transcription factor, due to insertional mutation occurring in a genome of cells when using the injection method.

Further, the present disclosure may realize the ETV2 transcription factor containing the magnetic nano-particles, thereby improving delivery efficiency of the ETV2 transcription factor to the target cell, and thereby overexpressing the ETV2 gene in the target cell without using a genetic material such as a virus or DNA plasmid.

The present disclosure may realize the pharmaceutical composition for treatment or prevention of an ischemic cardiovascular disease, the composition containing the ETV2 transcription factor. The present disclosure may realize the directly reprogrammed vascular endothelial cell that may be differentiated by the ETV2 transcription factor and may be used as a composition for cell therapeutic agent. Specifically, the pharmaceutical composition and the directly reprogrammed vascular endothelial cell according to the present disclosure may be used for new blood-vessel regeneration treatment of the diseases requiring inducing neovascularization in the ischemic tissue for the blood-vessel formation such as ischemic cardiovascular disease, brain blood-vessel disease, diabetes complications, and wound treatment.

The effects of the present disclosure are not limited to the effects as exemplified above. More various effects may be included herein.

MODES OF THE INVENTION

The advantages and features of the present disclosure and a method to achieve them will become apparent with reference to embodiments as described below in detail together with the accompanying drawings. However, the present disclosure is not limited to the embodiments as disclosed below but will be implemented in various different forms. Those embodiments are provided to ensure that the present disclosure is complete, and to completely inform the person of ordinary skill in the technical field to which the present disclosure belongs of the scope of the disclosure. The present disclosure is only defined by the scope of the claims.

Hereinafter, a structure of the ETV2 transcription factor according to one embodiment of the present disclosure will be described in detail with reference to FIG. 1A and FIG. 1B.

Figure 1A:
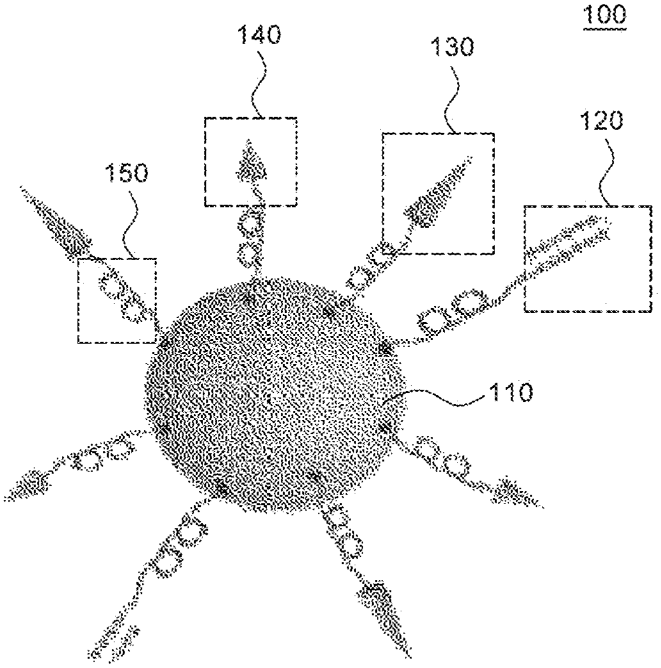
FIG. 1A and FIG. 1B illustrate a structure of an ETV2 transcription factor according to one embodiment of the present disclosure.
Figure 1B:
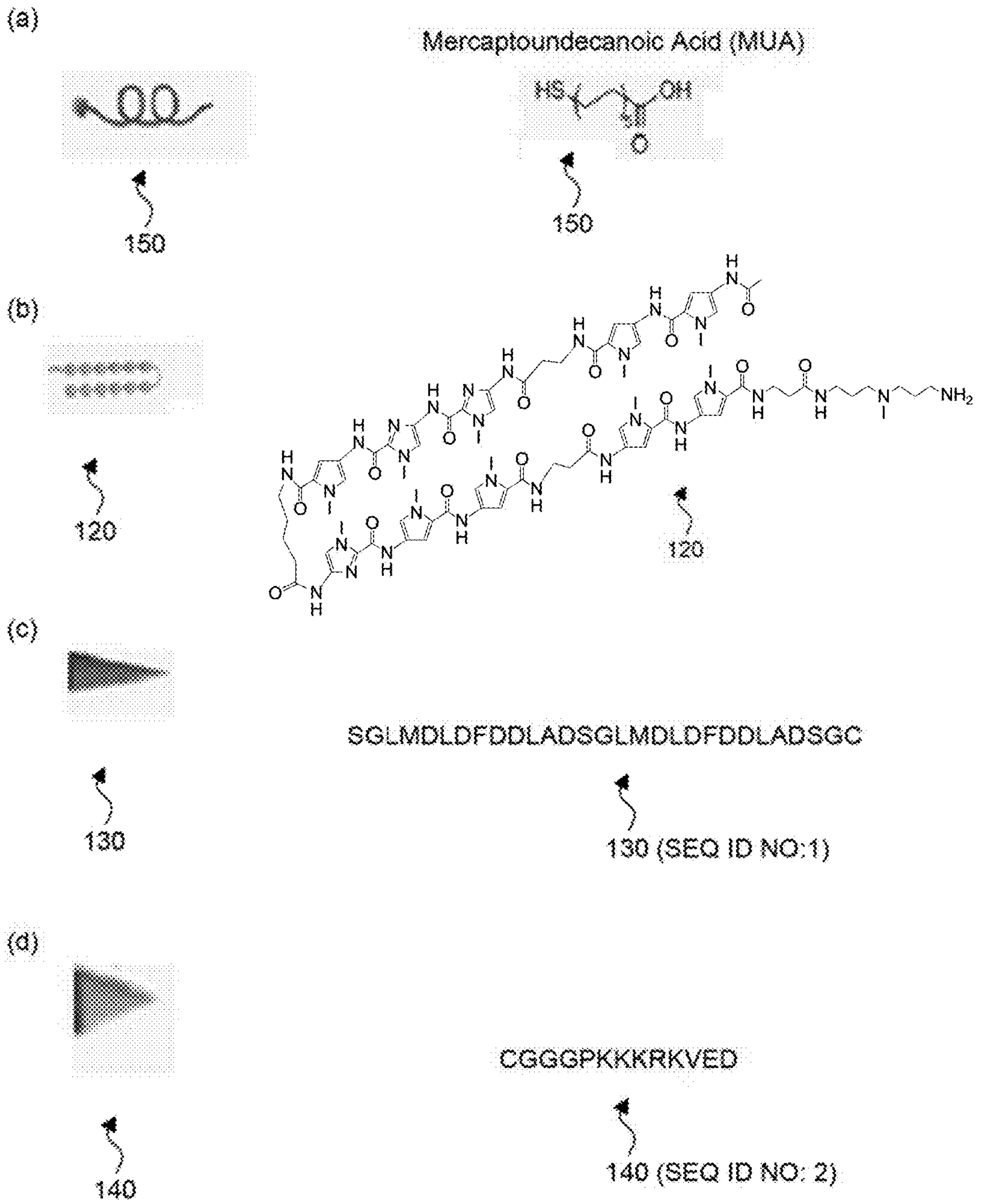

FIGS. 1A and 1B illustrate a structure of the ETV2 transcription factor according to one embodiment of the present disclosure.

Referring to FIG. 1A, an ETV2 transcription factor 100 according to the present disclosure includes functional polymers 120, 130 and 140 binding to a surface of a nano-particle 110, the polymers including polyamide 120 containing a DNA binding domain for an ETV2 gene, an active peptide 130 having a transcription activation domain of the ETV2 gene, and a nuclear localization signal peptide 140. The ETV2 transcription factor 100 further includes a linker 150 for attaching the functional polymers 120, 130 and 140 to the surface of the nano-particles 110. In this connection, the nano-particle 110 may be embodied as a magnetic nuclear gold nano-particle. However, the present disclosure is not limited thereto.

More specifically, referring to (a) of FIG. 1B, the linker 150 may be mercaptoundecanoic acid (MUA). In this connection, the MUA based linker 150 may be coupled to the functional polymers 120, 130 and 140 via EDC (1-ethyl-3-(3-dimethylaminopropyl)-carbodiimide) and/or NHS (N-hydroxy succinimide).

Referring to (b) of FIG. 1B, the polyamide 120 containing the DNA binding domain for the ETV2 gene may be a polyamide composed of a DNA binding domain for the ETV2 gene in the target cell. In this connection, the polyamide 120 may have a hairpin structure. However, the present disclosure is not limited thereto.

Referring to (c) of FIG. 1B, the active peptide 130 having the transcription activation domain of the ETV2 gene may be a polypeptide composed of 29 amino acids. In this connection, the active peptide 130 may have a homology of 70% or greater with the amino acid sequence represented by SEQ ID NO: 1. Preferably, the active peptide 130 may have 80% or greater homology with the amino acid sequence represented by SEQ ID NO: 1. More preferably, the active peptide 130 may have 90% or greater homology with the amino acid sequence represented by SEQ ID NO: 1. The active peptide 130 having such a configuration may be bound to the ETV2 gene to initiate transcription of the ETV2 gene, thereby activating the expression of the ETV2 gene in the cell.

Figure 2:
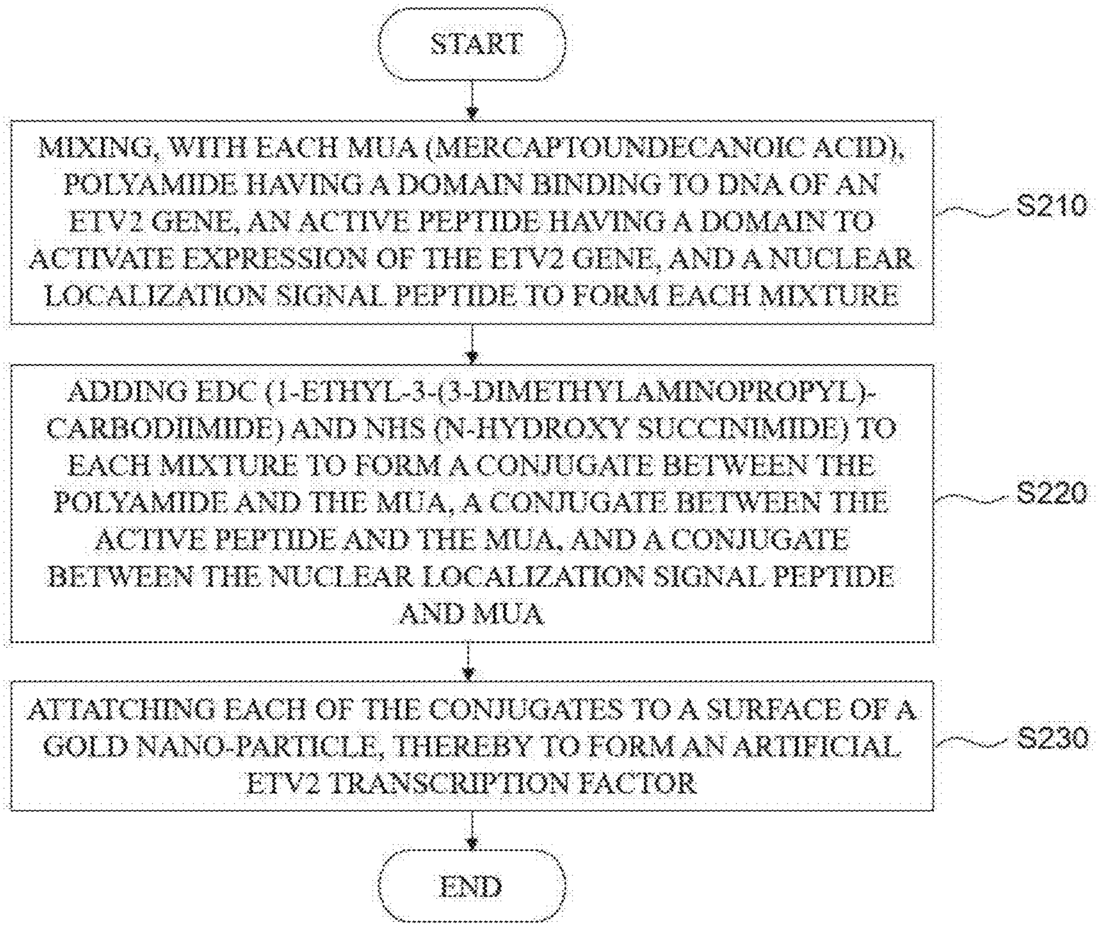
FIG. 2 shows a procedure of a method of preparing an ETV2 transcription factor according to one embodiment of the present disclosure.

Referring to (d) of FIG. 1B, the nuclear localization signal peptide 140 may be a polypeptide composed of 13 amino acids. In this connection, the nuclear localization signal peptide 140 may have a homology of 70% or greater with the amino acid sequence represented by SEQ ID NO: 2. Preferably, the nuclear localization signal peptide 140 may have 80% or greater homology to the amino acid sequence represented by SEQ ID NO: 2. More preferably, the nuclear localization signal peptide 140 may have 90% or greater homology with the amino acid sequence represented by SEQ ID NO: 2. The nuclear localization signal peptide 140 having this configuration may promote introduction of the ETV2 transcription factor 100 according to one embodiment of the present disclosure into the nucleus of the target cell. Referring to FIG. 2, a method of preparing the ETV2 transcription factor which is used in various examples of the present disclosure, will be described.

FIG. 2 shows a procedure of a method of preparing an ETV2 transcription factor according to one embodiment of the present disclosure.

Referring to FIG. 2, the ETV2 transcription factor according to one embodiment of the present disclosure may have a structure in which the polyamide containing the DNA binding domain for the ETV2 gene, the active peptide having a transcription activation domain of the ETV2 gene, and the nuclear localization signal peptide are attached onto the surface of the nano-particle.

More specifically, in order to prepare the ETV2 transcription factor, each of functional polymers composed of the polyamide the DNA binding domain for the ETV2 gene, the active peptide having the transcription activation domain of the ETV2 gene, and the nuclear localization signal peptide may be mixed with each MUA (S210). Next, EDC and NHS may be added to each mixture so that a conjugate between the polyamide and MUA, a conjugate between the active peptide and MUA, and a conjugate between the nuclear localization signal peptide and MUA may be formed, thereby attaching to the surface of the nano-particles, respectively (S220). Finally, the nano-particle according to the present disclosure may react with the conjugates, thereby to obtain the ETV2 transcription factor according to one embodiment of the present disclosure (S230).

According to a feature of the present disclosure, in the mixing step (S210), the polyamide having a content of 4 to 10% relative to the total amount of the functional polymers, the active peptide having a content of 20 to 30% relative to the total amount of the functional polymers, the nuclear localization signal peptides having a content of 60 to 75% relative to the total amount of the functional polymers may be mixed with the MUAs, respectively.

According to another feature of the present disclosure, in the preparation method of the ETV2 transcription factor, a step of introducing an epigenetic modulator including the SAHA derivative and the CTB derivative into the ETV2 transcription factor may be further performed, after the reaction step (S230). More specifically, in the step of introducing the epigenetic modulator, HDAC (Histone Deacetylase) activity may be inhibited by the SAHA derivative, and activity of HAT (Histone Acetyl Transferase) may be promoted by the CTB derivative.

According to the above preparation method of the ETV2 transcription factor, the ETV2 transcription factor which may induce neovascularization by activating the ETV2 transcription in the ischemic tissue, may be prepared. In another example, the ETV2 transcription factor preparation method is not limited to the above method. Depending on the structure of the ETV2 transcription factor, the ETV2 transcription factor preparation method may be modified diversely.

Hereinafter, the effect of the ETV2 transcription factor in accordance with the present disclosure on the neovascularization in the ischemic tissue will be described in detail based on various examples. In this connection, an ETV2 adenovirus (Ad-ETV2) to overexpress the ETV2 gene as a non-genome insertable medium was used as the ETV2 transcription factor in the evaluation. Therefore, the effect of the Ad-ETV2 which will be described later may be the same as the effect of the ETV2 transcription factor in accordance with the present disclosure.

Example 1: Formation of Directly Reprogrammed Vascular Endothelial Cells Using Ad-ETV2

Hereinafter, a result of formation of the directly reprogrammed vascular endothelial cell using Ad-ETV2 will be described with reference to FIGS. 3A to 3C. In this experiment, the formation of the directly reprogrammed vascular endothelial cell due to inoculation of Ad-ETV2 into human dermal fibroblast (HDF) was evaluated. However, the use of the Ad-ETV2 is not limited to the human dermal fibroblast. However, the effect resulting from using the Ad-ETV2 may be exhibited in more diverse cells or tissues.

More specifically, in the following experiment, after inoculation of Ad-ETV2 into a well in which human dermal fibroblast of $2\times10^5$ cells/well was cultured, an analysis related to vascular endothelial cell formation on the well for 9 days was performed.

Figure 3A:
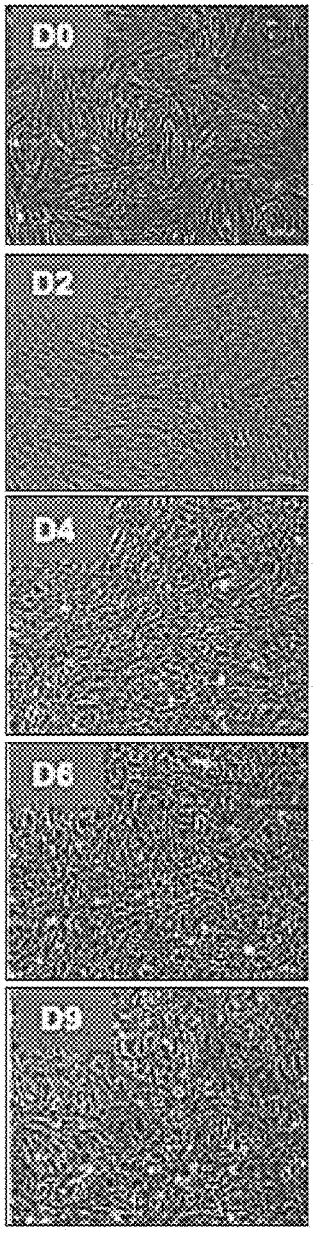
FIG. 3A is a result showing change in human dermal fibroblast due to inoculation of the ETV2 transcription factor according to one embodiment of the present disclosure.

FIG. 3A is a result showing change in human dermal fibroblast due to inoculation of the ETV2 transcription factor according to one embodiment of the present disclosure. FIG. 3B shows the expression level of vascular endothelial cell-specific gene in human dermal fibroblast due to inoculation of the ETV2 transcription factor, according to one embodiment of the present disclosure. FIG. 3C shows an expression level of vascular endothelial cell-specific protein in human dermal fibroblast due to inoculation of the ETV2 transcription factor, according to one embodiment of the present disclosure.

Referring to FIG. 3A, it may be identified that the human dermal fibroblast changes to a pebble form from 2 days after injection of the Ad-ETV2 into the human dermal fibroblast. In this connection, the pebble shape is a typical shape of the vascular endothelial cell. It appears that the shape becomes clearer over time toward the ninth day. That is, this result may mean that the human dermal fibroblast is reprogrammed into the endothelial cells using the Ad-ETV2.

Figure 3B:
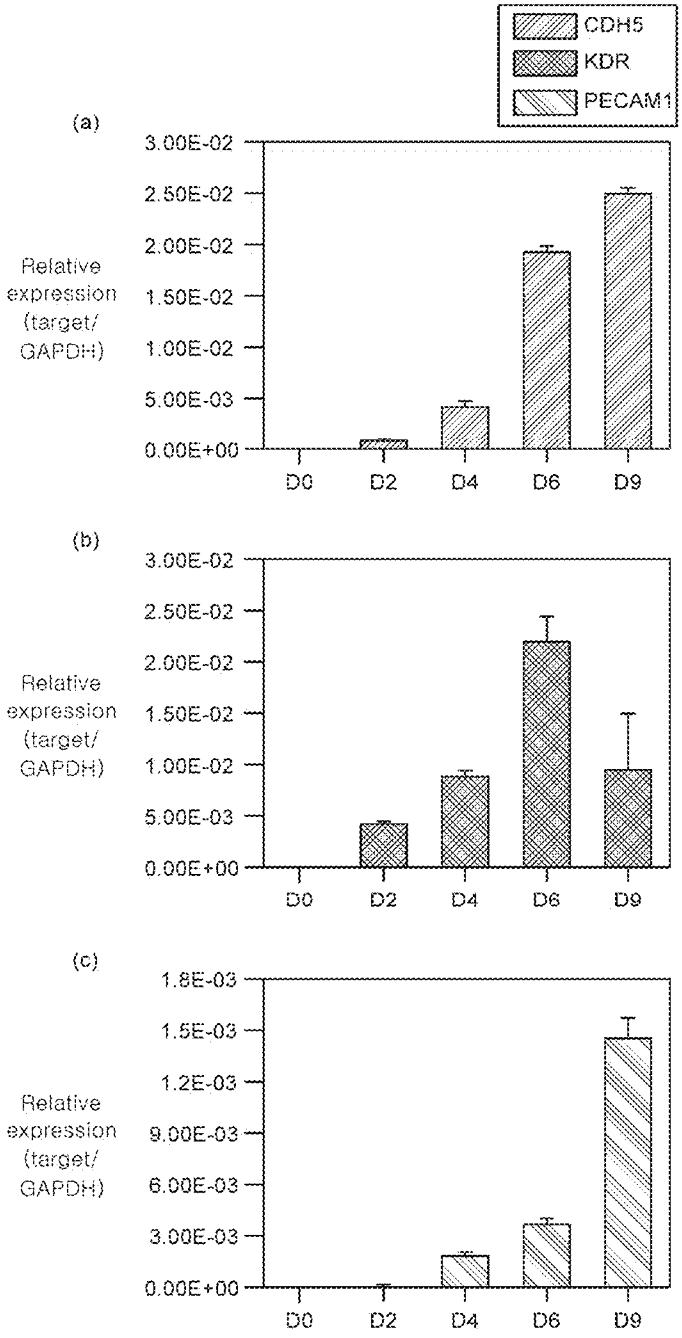
FIG. 3B shows an expression level of vascular endothelial cell-specific gene in human dermal fibroblast due to inoculation of the ETV2 transcription factor according to one embodiment of the present disclosure.

Referring to (a), (b), and (c) of FIG. 3B, results of observing the expression of a vascular endothelial cell-specific gene using qRT-PCR are shown. More specifically, the expression levels of CDH5 and KDR among vascular endothelial cell-specific genes gradually increase up to the sixth day. Furthermore, the increased expression levels of CDH5 and KDR are maintained up to the ninth day. In particular, the expression level of PECAM1 among vascular endothelial cell-specific genes is continuously increased and a significant increase in the expression level thereof is observed on the ninth day.

Figure 3C:
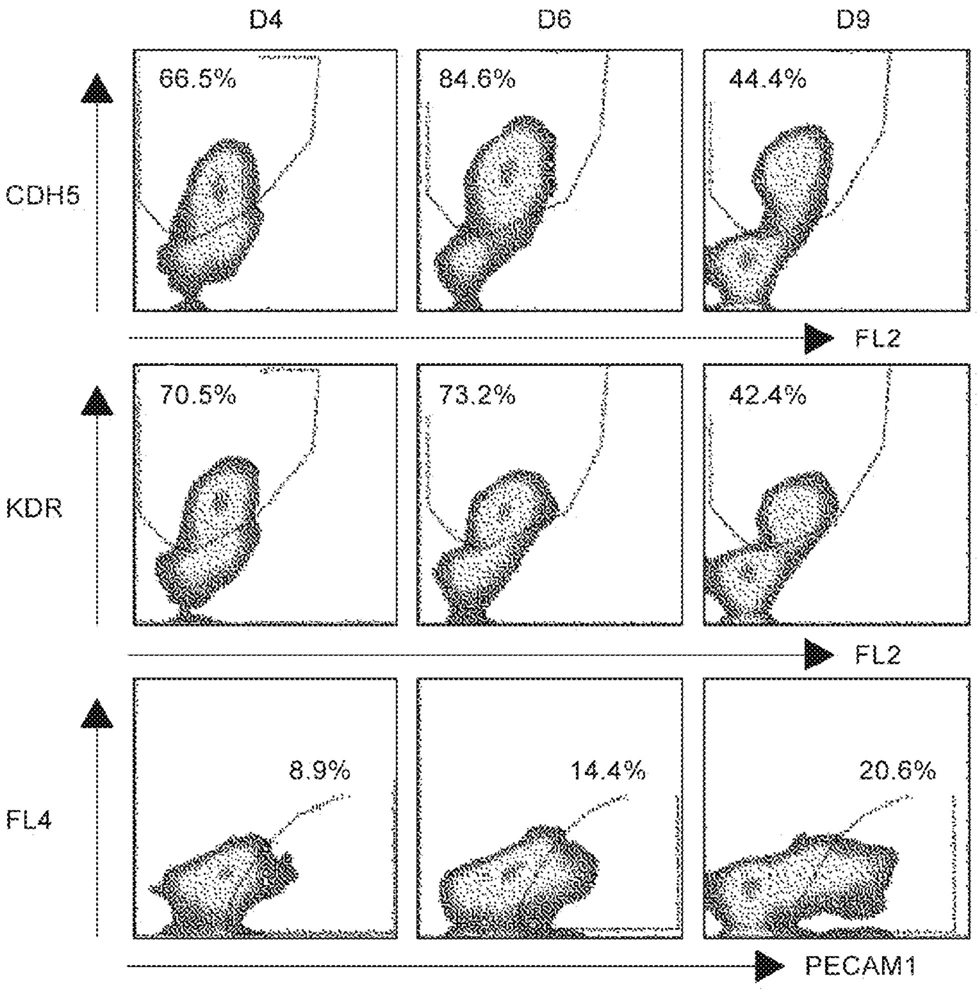
FIG. 3C shows an expression level of vascular endothelial cell-specific protein in human dermal fibroblast due to inoculation of the ETV2 transcription factor according to one embodiment of the present disclosure.

Referring to FIG. 3C, the result of analyzing the expression level of the vascular endothelial cell-specific protein via flow cytometry for human dermal fibroblast is shown. More specifically, 50% or more of the human dermal fibroblasts express CDH5 and KDR proteins on the fourth day. The highest expression levels of CDH5 and KDR proteins occur on the sixth day. Furthermore, it is identified that the expression level of PECAM1 protein in the human dermal fibroblast continues to increase up to the ninth day. This result may be consistent with the qRT-PCR result of FIG. 3C as described above.

The result of Example 1 above may mean that the injection of Ad-ETV2 to the somatic cell as the human dermal fibroblast is directly reprogrammed into the vascular endothelial cell without going through a pluripotent state. That is, the ETV2 transcription factor in accordance with the present disclosure may induce direct differentiation from the somatic cell to the vascular endothelial cell without going through a pluripotent state. Thus, the directly reprogrammed vascular endothelial cell may be applied as a cell therapeutic agent for the ischemic tissue.

Example 2: Evaluation of Directly Reprogrammed Vascular Endothelial Cells Induced by Ad-ETV2

Hereinafter, evaluation results of the directly reprogrammed vascular endothelial cells induced via injection of Ad-ETV2 will be described with reference to FIG. 4A to FIG. 4D.

More specifically, in the following experiment, in order to purify the directly reprogrammed vascular endothelial cells, cells (KDR positive) expressing KDR as a vascular endothelial cell-specific marker were separated using MACS (Magnetic-Activated Cell Sorting) on the 6th day after the injection of Ad-ETV2. In this connection, a cell (KDR negative) that does not express KDR was set as a control.

Figure 4A:
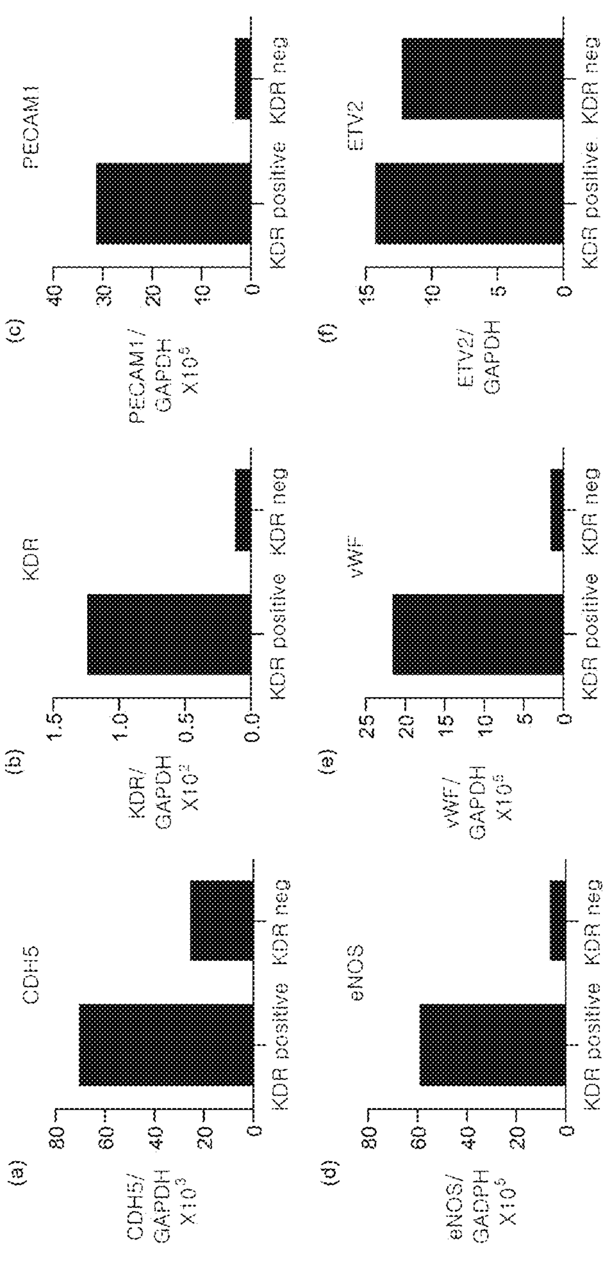
FIG. 4A shows an expression level of vascular endothelial cell-specific gene for KDR positive cells isolated after inoculation of the ETV2 transcription factor into human dermal fibroblast according to one embodiment of the present disclosure.
Figure 4B:
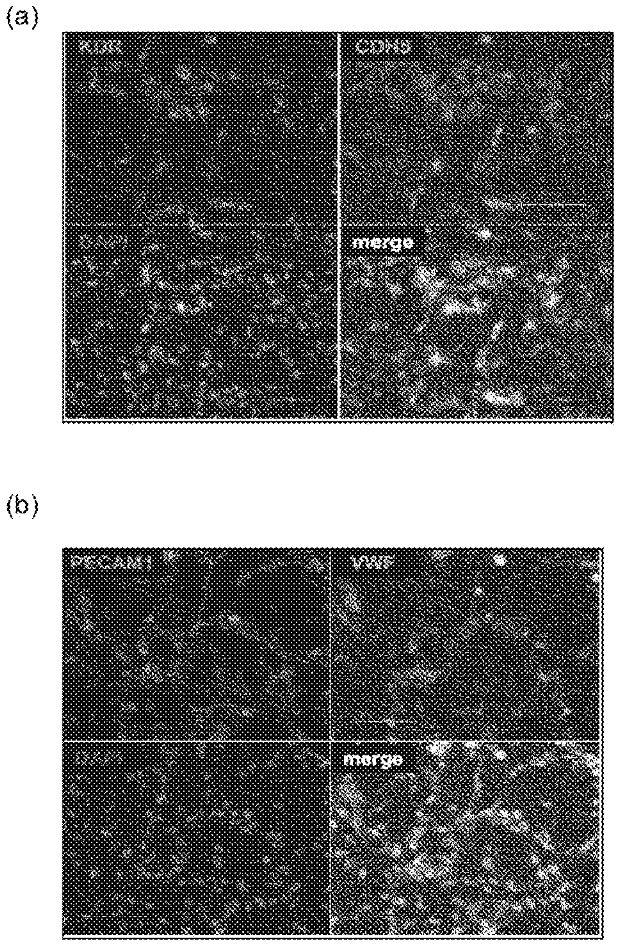
FIG. 4B shows results of an immunostaining method for KDR positive cells isolated after inoculation of the ETV2 transcription factor into human dermal fibroblast according to one embodiment of the present disclosure.
Figure 4C:
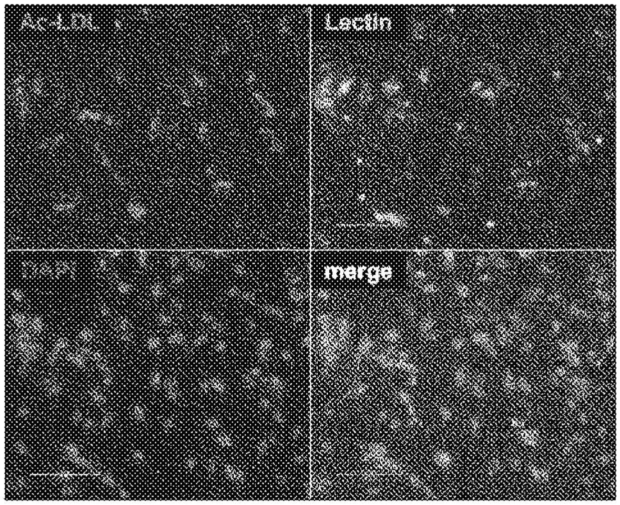
FIG. 4C shows a lectin adsorption level for KDR positive cells isolated after inoculation of the ETV2 transcription factor into human dermal fibroblast according to one embodiment of the present disclosure.

FIG. 4A shows the expression level of the vascular endothelial cell-specific gene for KDR positive cells isolated after inoculation of the ETV2 transcription factor into human dermal fibroblast according to one embodiment of the present disclosure. FIG. 4B shows the results of the immunostaining method for KDR positive cells isolated after inoculation of the ETV2 transcription factor into human dermal fibroblast according to one embodiment of the present disclosure. FIG. 4C shows the lectin adsorption level for KDR positive cells isolated after inoculation of the ETV2 transcription factor into human dermal fibroblast according to one embodiment of the present disclosure. FIG.

4D shows the comparison between the structures of KDR positive cells and KDR negative cells isolated after inoculation of the ETV2 transcription factor into human dermal fibroblast according to one embodiment of the present disclosure.

Referring to (a), (b), (c), (d), (e) and (f) of FIG. 4A, the results of the analysis of the expression of the vascular endothelial cell-specific gene for the KDR positive directly reprogrammed vascular endothelial cell using qRT-PCR are shown. More specifically, referring to (a), (b), (c), (d), and (e) of FIG. 4A, the expression levels of CDH5, KDR, PECAM1, eNOS, vWF as the vascular endothelial cell-specific genes in the KDR positive directly reprogrammed vascular endothelial cells are found to be significantly increased in contrast to those in the KDR negative cells. In one example, referring to (e) of FIG. 4A, the result of the increased expression level of the ETV2 in the KDR negative cells may indicate that the ETV2 expression level is increased due to the injection of Ad-ETV2 into the somatic cells before the separation of KDR positive or negative cells.

Referring to (a) and (b) of FIG. 4B, the results of the expression of vascular endothelial cell-specific protein in the KDR positive directly reprogrammed vascular endothelial cells are shown via immunocytochemistry. More specifically, it is identified that KDR, CDH5, PECAM1 and VWF as vascular endothelial cell-specific proteins are expressed in the KDR positive directly reprogrammed vascular endothelial cells.

Referring to FIG. 4C, acetylated-LDL (Ac-LDL) absorption and lectin adsorption as one of typical cell functional characteristics of vascular endothelial cells are observed in the KDR positive directly reprogrammed vascular endothelial cells.

Figure 4D:
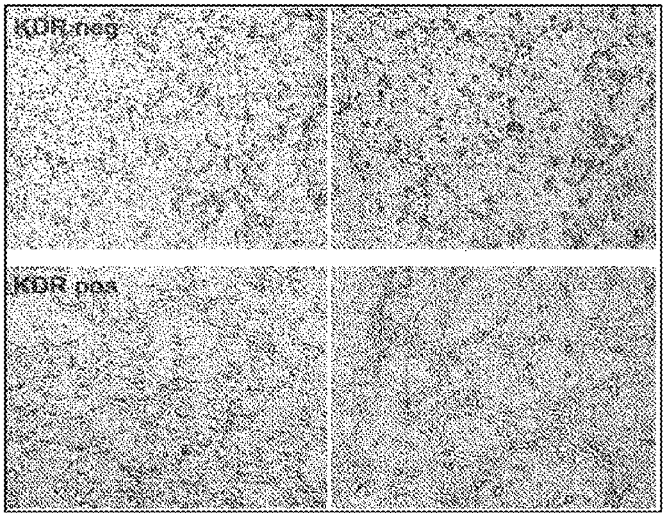
FIG. 4D shows a comparison between a structure of a KDR positive cell and a KDR negative cells isolated after inoculation of the ETV2 transcription factor into human dermal fibroblast according to one embodiment of the present disclosure.

Referring to FIG. 4D, it is identified that the KDR positive (KDR pos) directly reprogrammed vascular endothelial cells form a tubular structure when cultured in Matrigel, which is not the case in KDR negative (KDR neg) cell.

According to the result of Example 2 above, injection of Ad-ETV2 into human dermal fibroblast induces overexpression of the ETV2. As a result, the directly reprogrammed vascular endothelial cells could be obtained. That is, the ETV2 transcription factor in accordance with the present disclosure may induce direct differentiation from a somatic cell to a vascular endothelial cell without going through a pluripotent state.

Example 3: Treatment Effect on Ischemic Tissue by Directly Reprogrammed Vascular Endothelial Cells Induced by Ad-ETV2

Hereinafter, with reference to FIGS. 5A and 5B, the therapeutic effect on ischemic tissue by the directly reprogrammed vascular endothelial cells induced via injection of Ad-ETV2 will be described.

More specifically, in this experiment, directly reprogrammed vascular endothelial cells isolated purely using the method as described above in Example 2 were injected into an ischemia boarder zone of a heart of a myocardial infarction-induced athymic nude mice model. In this connection, the myocardial infarction-induced model was obtained by ligating a left anterior descending artery (LAD) of a left ventricle. In one example, in this experiment, synthetic biomaterial PA-RGDS (CH3(CH2)14CONH-GTA-GLIGQ-RGDS) (RGDS (SEQ ID NO: 3) conjugated Peptide Amphiphile) was injected into the directly reprogrammed vascular endothelial cells in order to increase a remaining time of the directly reprogrammed vascular endothelial cells. In this connection, a myocardial infarction-induced model to which PBS (phosphate buffered saline) was injected was set as a control.

Figure 5A:
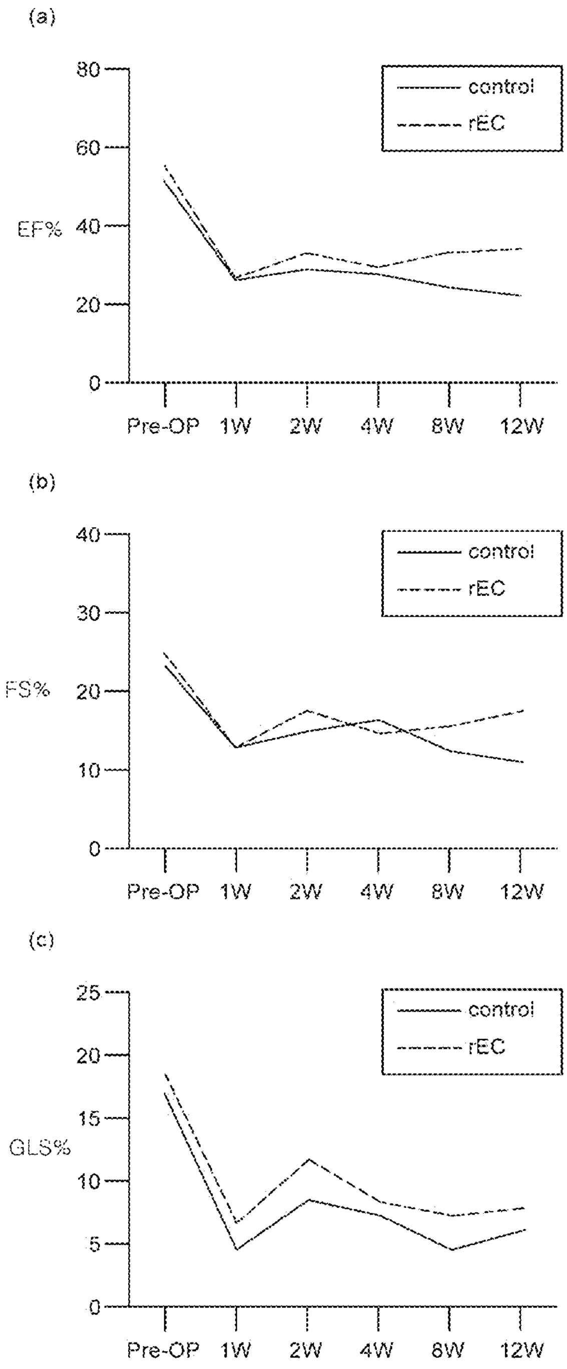
FIG. 5A is a result showing change in a cardiac function due to inoculation of the directly reprogrammed vascular endothelial cells induced by the ETV2 transcription factor according to one embodiment of the present disclosure.

FIG. 5A is a result showing change in a cardiac function due to inoculation of the directly reprogrammed vascular endothelial cells induced by the ETV2 transcription factor, according to one embodiment of the present disclosure. FIG. 5B shows results of an immunostaining method for a cardiac tissue due to inoculation of the directly reprogrammed vascular endothelial cells induced by the ETV2 transcription factor, according to one embodiment of the present disclosure.

Referring to (a), (b) and (c) of FIG. 5A, the results of the cardiac function recovery based on echocardiography are shown. In this connection, it is identified based on the results of observing the cardiac function of the myocardial infarction-induced models (reprogrammed EC, rEC) at 1, 2, 4, 8, and 12 weeks from the time of the injection of the directly reprogrammed vascular endothelial cells induced by the ETV2 transcription factor, that the myocardial infarction-induced model (rEC) having the directly reprogrammed vascular endothelial cells injected thereto have recovered ejection fraction (EF), fractional shortening (FS) and global longitudinal strain (GLS), compared to the control.

More specifically, it is identified that the cardiac function of the myocardial infarction-induced models having the directly reprogrammed vascular endothelial cells injected thereto is similar to that of the control up to the fourth week. However, as the time lapses toward 8-th week and 12-th week, the control has the weakened cardiac function. However, as the time lapses toward 8-th week and 12-th week, the myocardial infarction-induced model having the directly reprogrammed vascular endothelial cells injected thereto maintains the cardiac function or has a recovered cardiac function to a pre-operation (pre-OP) level. These results may mean that the directly reprogrammed vascular endothelial cells serve to prevent the deterioration of the cardiac function due to the ischemic heart disease.

Figure 5B:
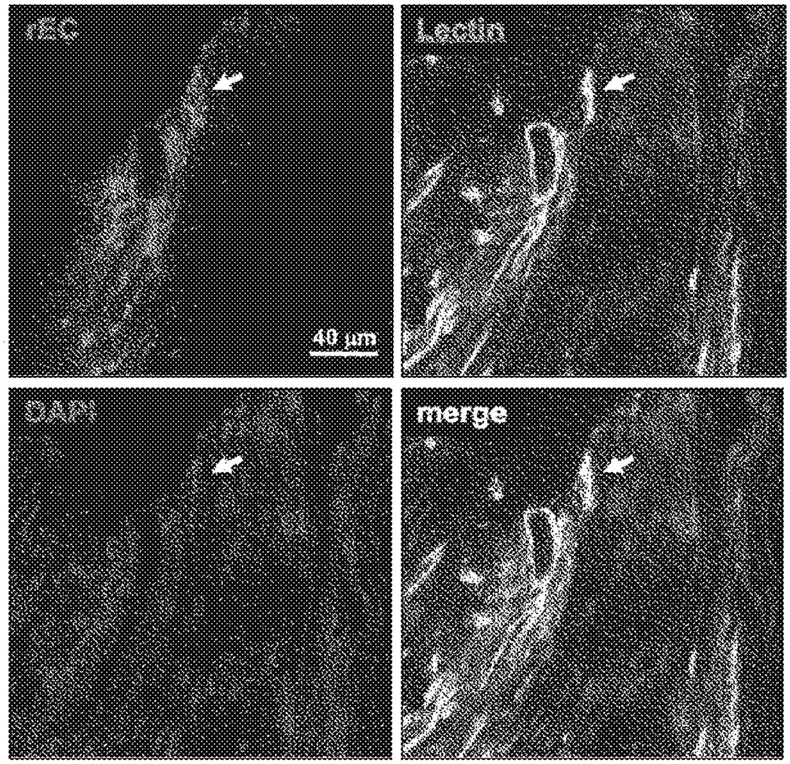
FIG. 5B shows results of an immunostaining method for a cardiac tissue due to inoculation of the directly reprogrammed vascular endothelial cells induced by the ETV2 transcription factor according to one embodiment of the present disclosure.

Referring to FIG. 5B, the results of evaluating the ability to form the blood-vessel in vivo using a histological assay are shown. In this connection, this evaluation was performed by injecting lectin labeled with green fluorescent substance (Fluorescein isothiocyanate, FITC) into the perfusion of the myocardial infarction-induced model having the directly reprogrammed vascular endothelial cells injected thereto at the 12-th week to label the blood vessel with the green fluorescent substance, and then sacrificing the model, and then examining a cardiac tissue of the model using a confocal fluorescence microscope. The directly reprogrammed vascular endothelial cells were labeled with a red fluorescent substance (CM-DiI).

More specifically, it is identified that, in the cardiac tissue of the myocardial infarction-induced model to which the directly reprogrammed vascular endothelial cells were injected, the directly reprogrammed vascular endothelial cells that emit red light are present even at 12 weeks from the injection of the directly reprogrammed vascular endothelial cells thereto. Furthermore, it is observed that these directly reprogrammed vascular endothelial cells are present around the blood-vessels that emit green light due to the lectin labeled with FITC. Furthermore, as shown by an arrow, the clearly labeled blood-vessel in a region where the directly reprogrammed vascular endothelial cells gather together may mean that the injected directly reprogrammed vascular endothelial cell is involved in neovascularization.

According to the above result of Example 3, it is identified that the directly reprogrammed vascular endothelial cells induced by the Ad-ETV2 induce neovascularization. In other words, the directly reprogrammed vascular endothelial cells induced by the injection of the ETV2 transcription factor in accordance with the present disclosure may induce neovascularization in the ischemic tissue, thereby to prevent the cardiac function from weakening, and to contribute to the recovery of the ischemic cardiac function. Therefore, the ETV2 transcription factor and the directly reprogrammed vascular endothelial cell induced by the ETV2 transcription factor may be used as a pharmaceutical composition for treatment and prevention of an ischemic heart disease.

Example 4: Therapeutic Effect of Ad-ETV2 on Ischemic Tissue

Hereinafter, with reference to FIG. 6A to FIG. 6E, the effect of treatment of the ischemic tissue via direct injection of Ad-ETV2 will be described.

More specifically, in this experiment, Ad-ETV2 ($5\times10^7$ infectious viral particles/50 μl/mouse) was injected into the cardiac ischemia border area of each of the myocardial infarction induced nude mouse model (acute myocardial infarction, MI) obtained by the method as described in Example 3 and a normal nude mouse model (non-acute myocardial infarction, Non MI) in which the myocardial infarction was not induced. In this connection, a myocardial infarction-induced model and a myocardial infarction non-induced model to which PBS (phosphate buffered saline) was injected at the same dose were set as controls.

Figure 6A:
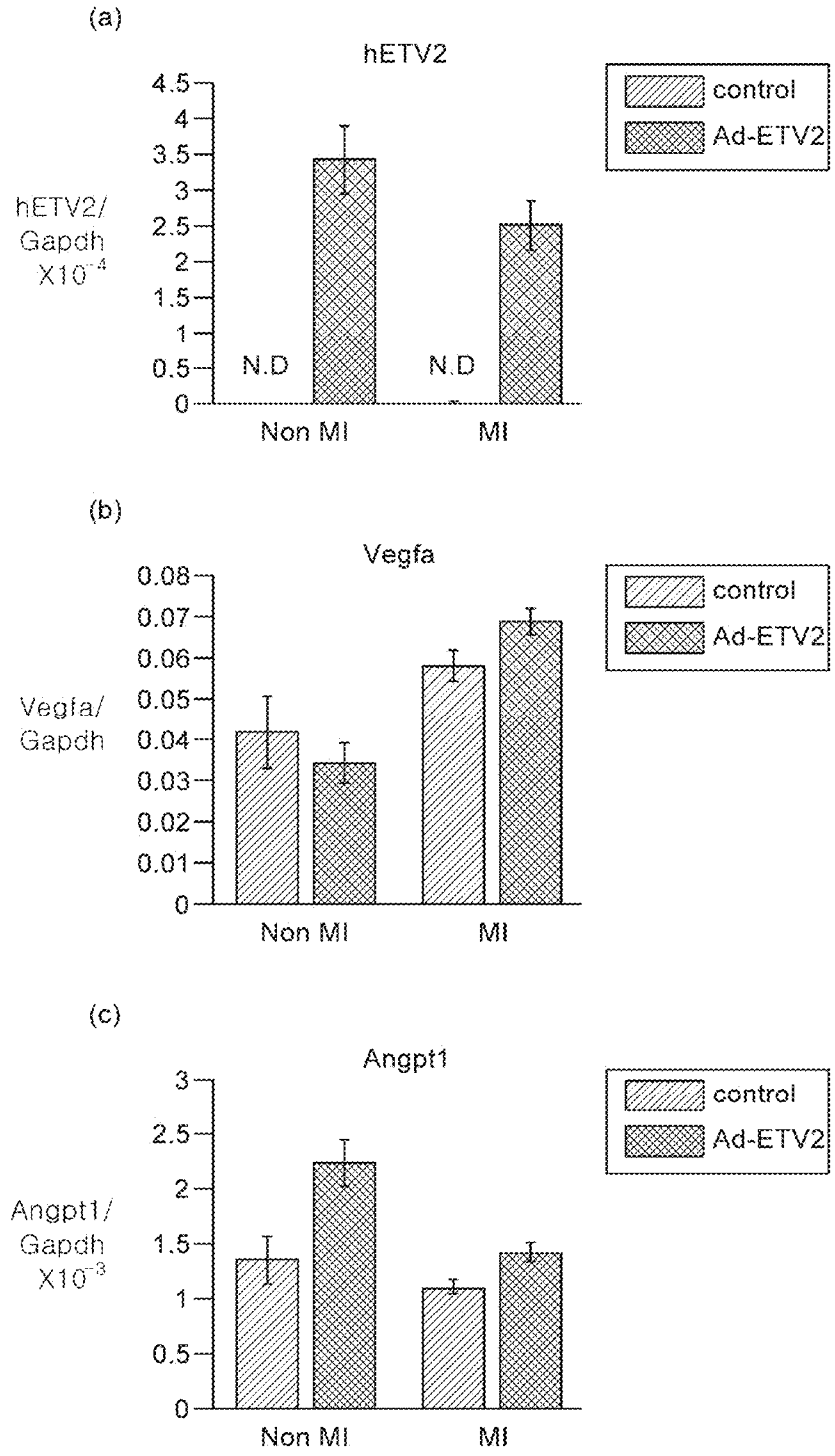
FIG. 6A shows an expression level of a gene related to neovascularization in the ischemic tissue due to inoculation or non-inoculation of the ETV2 transcription factor according to one embodiment of the present disclosure.
Figure 6B:
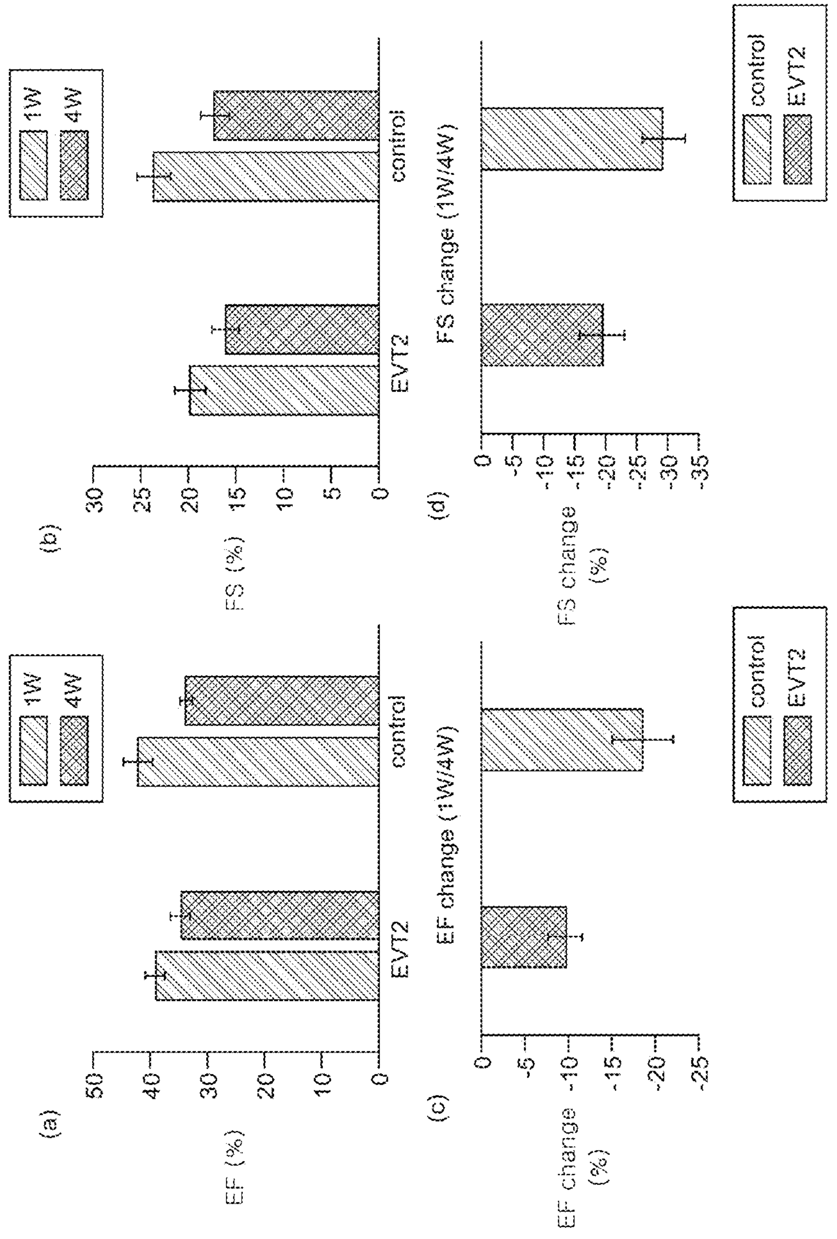
FIG. 6B is a result showing change in a cardiac function due to inoculation or non-inoculation of the ETV2 transcription factor according to one embodiment of the present disclosure.
Figure 6C:
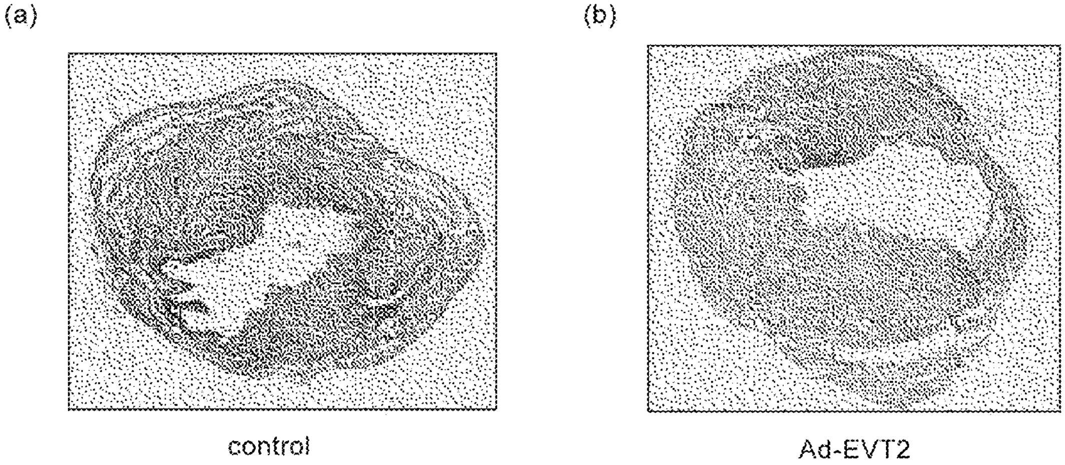
FIG. 6C and FIG. 6D show results of analyzing a degree of fibrosis for an ischemic cardiac tissue due to inoculation or non-inoculation of the ETV2 transcription factor according to one embodiment of the present disclosure.
Figure 6D:
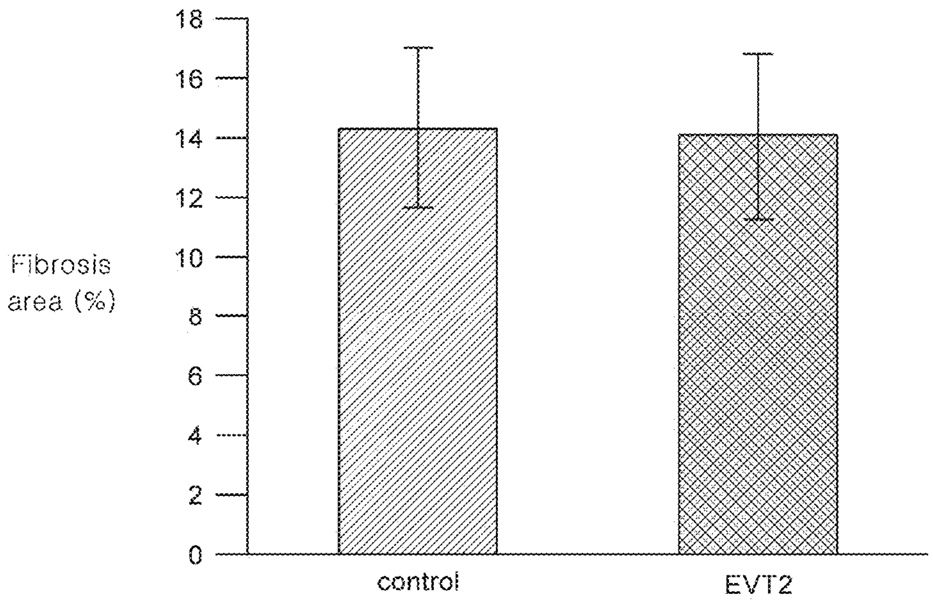
Figure 6E:
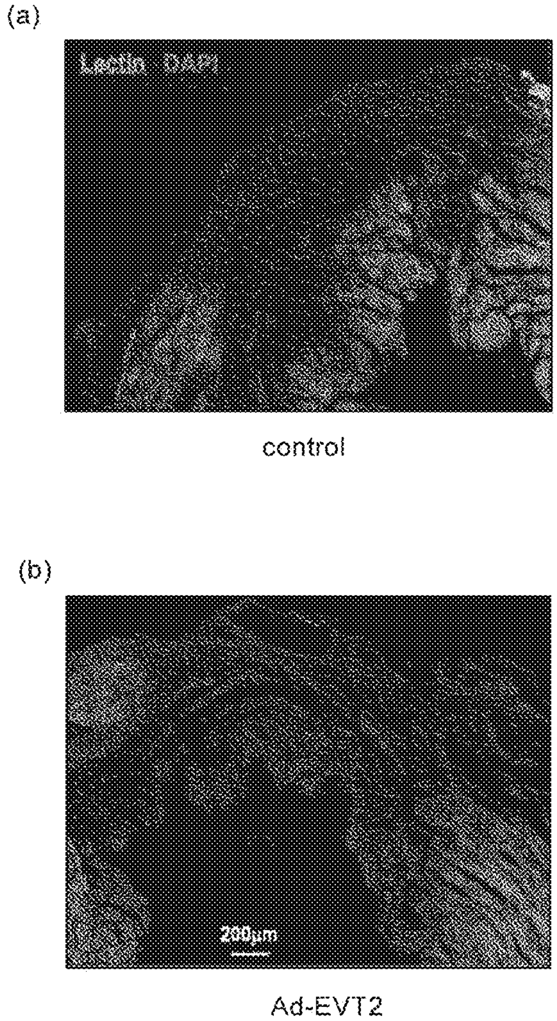
FIG. 6E shows results of a cardiovascular distribution analysis for an ischemic cardiac tissue due to inoculation or non-inoculation of the ETV2 transcription factor according to one embodiment of the present disclosure.

FIG. 6A shows an expression level of a gene related to neovascularization in the ischemic tissue due to inoculation or non-inoculation of the ETV2 transcription factor according to one embodiment of the present disclosure. FIG. 6B is a result showing change in a cardiac function due to inoculation or non-inoculation of the ETV2 transcription factor according to one embodiment of the present disclosure. FIG. 6C and FIG. 6D show results of analyzing a degree of fibrosis for an ischemic cardiac tissue due to inoculation or non-inoculation of the ETV2 transcription factor according to one embodiment of the present disclosure. FIG. 6E shows results of a cardiovascular distribution analysis for an ischemic cardiac tissue due to inoculation or non-inoculation of the ETV2 transcription factor according to one embodiment of the present disclosure.

Referring to (a), (b), and (c) of FIG. 6A, the cardiac tissue was extracted from each of the myocardial infarction-induced model and the myocardial infarction non-induced model on the third day from the injection of the Ad-ETV2, and RNA was extracted therefrom. Then, expression levels of ETV2, Vegfa and Angptl were measured using qRT-PCR. In this connection, Vegfa and Angptl may be genes related to neovascularization. More specifically, it is identified that the human ETV2 is expressed only in the heart of the models (Non MI and MI) having the Ad-ETV2 injected thereto. Furthermore, in the heart of the myocardial infarction-induced model injected with the Ad-ETV2, the expression levels of the neovascularization-related genes Vegfa and Angptl are increased, compared to those of the controls. These results may indicate that expression of the neovascularization-related gene is induced due to the ETV2 overexpression resulting from the Ad-ETV2 injection.

Referring to (a), (b), (c), and (d) of FIG. 6B, the results of analyzing the cardiac function of the models using echocardiography at the first week and the fourth week from the time of the injection are shown. More specifically, it is identified that EF and FS decrease at the fourth week, compared to the first week in both the control models and the Ad-ETV2-injected models. However, in the Ad-ETV2-injected model, the reduction of EF and FS levels is smaller than that in the control. These results may mean that ETV2 overexpression induced by the injection of the Ad-ETV2 prevents the cardiac function from being weakened due to ischemic symptoms.

Referring to FIGS. 6C and 6D, the results of performing a tissue test of an ischemic cardiac tissue collected from each model at the fourth week from the injection of the Ad-ETV2 are shown. In this connection, Masson's Trichrome staining and H & E staining were performed to check whether fibrosis occurred in the left ventricle of the heart. In one example, collagen in the fibrous portion may be dyed blue. More specifically, it is identified that the control and the Ad-ETV2-injected model (Ad-ETV2) have similar sizes of the fibrous portions in the cardiac tissue.

In one example, referring to (a) and (b) of FIG. 6E, examination results to check the cardiovascular distribution are shown in which lectin labeled with green fluorescent substance (Fluorescein isothiocyanate, FITC) is injected to the perfusion of each of the control model (control) and the Ad-ETV2-injected model (Ad-ETV2) to label the blood vessel with the green fluorescent substance, and then the blood-vessels of the heart of the models are examined using a confocal fluorescence microscope. More specifically, the blood-vessel stained in green is not found in the ischemic tissue part in the control, whereas the blood-vessel stained in green is found in the ischemic tissue area in the Ad-ETV2-injected model (Ad-ETV2) injected with Ad-ETV2. These results may indicate that the neovascularization was induced due to the ETV2 overexpression resulting from the Ad-ETV2 injection into the ischemic tissue.

According to the results of Example 4 as mentioned above, it is identified that the Ad-ETV2 functions as a direct injection that promotes regeneration of an ischemic tissue. Thus, the ETV2 transcription factor in accordance with the present disclosure may be embodied as a composition that may be directly injected into an ischemic tissue. Furthermore, the pharmaceutical composition for treatment or prevention of an ischemic cardiovascular disease, the composition containing the TV2 transcription factor in accordance with the present disclosure may be injected directly into an ischemic tissue to induce the neovascularization.

The present disclosure may realize the ETV2 transcription factor and the preparation method thereof as disclosed in Example 1 to Example 4 and may realize an efficient differentiation method into vascular endothelial cells, in which the skin fibroblast as a source cell may be directly reprogrammed to vascular endothelial cells without going through a pluripotent state.

Thus, according to the present disclosure, the side effects of the blood-vessel regeneration treatment and the slight therapeutic effect as caused by potential risk factors of pluripotent stem cells, such as the development of tumors and abnormal tissues, the use of animal components used in differentiation processes, and the low differentiation into vascular endothelial cells may be removed.

Furthermore, the present disclosure may realize the ETV2 transcription factor clinically applied directly to the ischemic tissue to overexpress the ETV2 gene. Thus, the ETV2 transcription factor according to the present disclosure has an effect of solving the problem in a clinical application of a retrovirus or lentivirus-mediated gene injection method used conventionally for overexpression of the transcription factor, due to insertional mutation occurring in a genome of cells when using the injection method.

The present disclosure may realize the pharmaceutical composition for treatment or prevention of an ischemic cardiovascular disease, the composition containing the ETV2 transcription factor. The present disclosure may realize the directly reprogrammed vascular endothelial cell that may be differentiated by the ETV2 transcription factor and may be used as a composition for cell therapeutic agent. Specifically, the pharmaceutical composition and the directly reprogrammed vascular endothelial cell may be used for new blood-vessel regeneration treatment of the diseases requiring inducing neovascularization in the ischemic tissue for the blood-vessel formation such as ischemic cardiovascular disease, brain blood-vessel disease, diabetes complications, and wound treatment.

Further, the effects of the present disclosure are not limited to the effects exemplified above. More various effects may be included herein. For example, the present disclosure may realize the ETV2 transcription factor containing the magnetic nano-particles, thereby improving delivery efficiency of the ETV2 transcription factor to the target cell, and thereby overexpressing the ETV2 gene in the target cell without using a genetic material such as a virus or DNA plasmid.

| Sequence Listing Free Text |
| --- |
| Sequence listing 1<br>Ser Gly Leu Met Asp Leu Asp Phe Asp Asp Leu Ala Asp Ser Gly Leu<br>5 10 15<br><br>Met Asp Leu Asp Phe Asp Asp Leu Ala Asp Ser Gly Cys<br>20 25<br><br>Sequence listing 2<br>Cys Gly Gly Gly Pro Lys Lys Lys Arg Lys Val Glu Asp<br>5 10<br><br>Sequence listing 3<br>Arg Gly Asp Ser |

[National R & D Project Supporting Present Invention]

Project Assignment No.: HI15C2782

Department Name: Ministry of Health and Welfare

Research Management Agency: Korea Health Industry Development Institute

Research Project Name: Advanced Medical Technology Development/Stem Cell, Regenerative Medical Infrastructure Development International Cooperation Project Title: Development of direct reprogramming method into vascular endothelial cells using nanoparticles Contribution Percentage: 1/1

Host Organization: Yonsei University Industry-Academic Cooperation Foundation

Research Period: 2015.12.01 to 2019.11.3

The invention claimed is:

1. An ETV2 transcription factor comprising:

a polyamide having a DNA binding domain for an ETV2 gene;

a nuclear localization signal peptide comprising SEQ ID NO: 2; and a nano-particle onto which the polyamide and the nuclear localization signal peptide are attached, wherein the polyamide has the following structure:

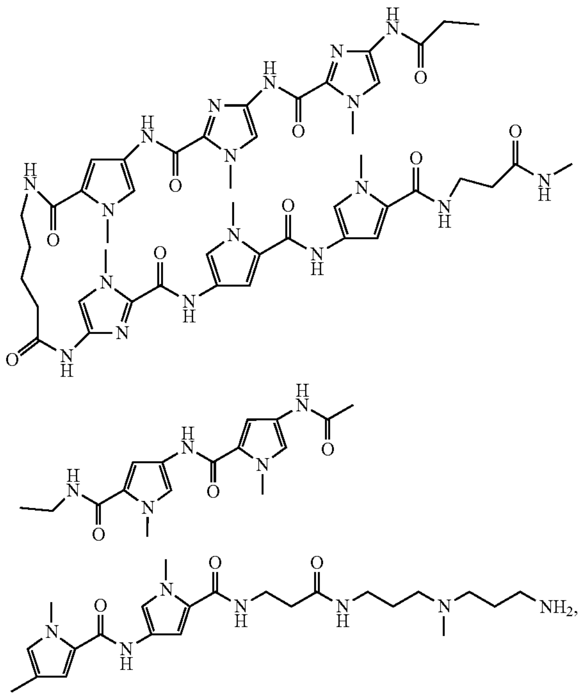

and wherein the polyamide binds to a binding site of the ETV2 gene.

2. The ETV2 transcription factor of claim 1, further comprising a plurality of MUAs (mercaptoundecanoic acids), wherein the plurality of MUAs are configured to link at least one of the polyamide and the nuclear localization signal peptide to the nano-particle.

3. The ETV2 transcription factor of claim 1, wherein the polyamide has a surface area of 4 to 10% of an entire surface area of the nano-particle.

4. The ETV2 transcription factor of claim 1, wherein the nuclear localization signal peptide has a surface area of 60 to 75% of an entire surface area of the nano-particle.

5. The ETV2 transcription factor of claim 1, wherein the nano-particle is selected from the group consisting of gold nano-particle, a magnetic gold nano-particle, a silver nano-particle, and a tin nano-particle.

6. The ETV2 transcription factor of claim 1, wherein the nano-particle comprises a magnetic gold nanoparticle, and wherein the ETV2 transcription factor is configured to be tracked non-invasively via Raman/dark-field imaging.

7. The ETV2 transcription factor of claim 1, wherein the polyamide has a surface area of 9% relative to an entire surface area of the nanoparticle, and wherein the nuclear localization signal peptide has a surface area of 68% relative to the entire surface area of the nanoparticle.

8. The ETV2 transcription factor of claim 1, wherein the polyamide has a surface area of 7 to 9% relative to the entire surface area of the nanoparticle, and wherein the nuclear localization signal peptide has a surface area of 66 to 69% relative to the entire surface area of the nanoparticle.

9. A pharmaceutical composition for treatment or prevention of an ischemic cardiovascular disease, the composition comprising the ETV2 transcription factor according to any of claims 1, 3, 4 or 5.

10. The pharmaceutical composition of claim 9, wherein the composition further comprises vascular endothelial cells differentiated by the ETV2 transcription factor.

* * * * *

SEQUENCE LISTING

```
<160> NUMBER OF SEQ ID NOS: 3

<210> SEQ ID NO 1
<211> LENGTH: 29
<212> TYPE: PRT
<213> ORGANISM: Artificial Sequence
<220> FEATURE:
<223> OTHER INFORMATION: Synthesized

<400> SEQUENCE: 1

Ser Gly Leu Met Asp Leu Asp Phe Asp Asp Leu Ala Asp Ser Gly Leu
1               5                   10                  15

Met Asp Leu Asp Phe Asp Asp Leu Ala Asp Ser Gly Cys
            20                  25


<210> SEQ ID NO 2
<211> LENGTH: 13
<212> TYPE: PRT
<213> ORGANISM: Artificial Sequence
<220> FEATURE:
<223> OTHER INFORMATION: Synthesized
```

-continued

```
<400> SEQUENCE: 2

Cys Gly Gly Gly Pro Lys Lys Lys Arg Lys Val Glu Asp
1               5                   10


<210> SEQ ID NO 3
<211> LENGTH: 4
<212> TYPE: PRT
<213> ORGANISM: Artificial Sequence
<220> FEATURE:
<223> OTHER INFORMATION: Synthesized

<400> SEQUENCE: 3

Arg Gly Asp Ser
1
```